(12) United States Patent
Takeuchi et al.

(10) Patent No.: US 10,245,238 B2
(45) Date of Patent: Apr. 2, 2019

(54) COMPOSITION FOR ORAL INTAKE

(71) Applicants: THERAVALUES CORPORATION, Chiyoda-ku (JP); Hirofumi Takeuchi, Gifu-shi (JP)

(72) Inventors: Hirofumi Takeuchi, Gifu (JP); Kohei Tahara, Gifu (JP); Atsushi Imaizumi, Hino (JP); Tsukasa Takahashi, Sayama (JP); Takato Matsui, Akita (JP); Hitomi Ozawa, Yokohama (JP)

(73) Assignees: THERAVALUES CORPORATION, Chiyoda-ku (JP); Hirofumi Takeuchi, Gifu-shi (JP)

( * ) Notice: Subject to any disclaimer, the term of this patent is extended or adjusted under 35 U.S.C. 154(b) by 40 days.

(21) Appl. No.: 15/305,143

(22) PCT Filed: May 14, 2015

(86) PCT No.: PCT/JP2015/063846
§ 371 (c)(1),
(2) Date: Oct. 19, 2016

(87) PCT Pub. No.: WO2015/174475
PCT Pub. Date: Nov. 19, 2015

(65) Prior Publication Data
US 2017/0239194 A1    Aug. 24, 2017

(30) Foreign Application Priority Data

May 15, 2014  (JP) .............................. 2014-101044

(51) Int. Cl.
*A61K 31/12* (2006.01)
*A61K 36/9066* (2006.01)
*A61K 9/00* (2006.01)

(52) U.S. Cl.
CPC ............ *A61K 31/12* (2013.01); *A61K 9/0053* (2013.01); *A61K 36/9066* (2013.01)

(58) Field of Classification Search
CPC .. A61K 31/12; A61K 47/4823; A61K 9/0053; A61K 36/9066
USPC ........................... 514/679; 424/400; 977/773
See application file for complete search history.

(56) References Cited

U.S. PATENT DOCUMENTS

| | | | |
|---|---|---|---|
| 4,999,205 A | 3/1991 | Todd, Jr. | |
| 2003/0091643 A1 | 5/2003 | Friesen et al. | |
| 2010/0029667 A1 | 2/2010 | Ketner et al. | |
| 2011/0212142 A1* | 9/2011 | Chaniyilparampu | ........... A61K 9/0048 424/400 |
| 2012/0076838 A1 | 3/2012 | Kim et al. | |
| 2013/0237609 A1 | 9/2013 | Edgar et al. | |
| 2013/0303628 A1 | 11/2013 | Breitenbach et al. | |
| 2014/0175686 A1 | 6/2014 | Kim et al. | |

FOREIGN PATENT DOCUMENTS

| | | |
|---|---|---|
| EP | 2 436 377 A2 | 4/2012 |
| JP | 3-97761 A | 4/1991 |
| JP | 7-291854 | 11/1995 |
| JP | 2000-281561 A | 10/2000 |
| JP | 2004-534812 A | 11/2004 |
| JP | 2005-41817 A | 2/2005 |
| JP | 2008-100997 A | 5/2008 |
| JP | 2009-263638 A | 11/2009 |
| JP | 2010-260816 A | 11/2010 |
| JP | 2012-527491 A | 11/2012 |
| JP | 2013-237752 | 11/2013 |
| JP | 2014-503470 A | 2/2014 |
| WO | 97-006781 | 2/1997 |
| WO | 2013/058751 A1 | 4/2013 |

OTHER PUBLICATIONS

Extended Search Report dated Oct. 13, 2017 in European Patent Application No. 15792660. 1.
Sav A. K. et al., "Dissolution rate enhancement of Curcumin by solid dispersion technique using hydrophilic polymers and in vitro characterization", Journal of Pharmaceutical Sciences, XP002774279, vol. 7, No. 4, 2012, pp. 263-280.
Pranali Waghmare, et al. "Solubility Enhancement of Curcumin Using HPMC K 15M by Solvent Change Precipitation Method", IJARPB (International Journal of Advanced Research in Pharmaceutical & Bio Sciences), 2014, 4 (2) , XP55411202, pp. 1-7 http://www.ijarpb.com.
Pamela Maher, et al., "A pyrazole derivative of curcumin enhances memory" Neurobiology of Aging, vol. 31, 2010, pp. 706-709 (Submitting complete copy).
International Search Report dated Aug. 18, 2015 in PCT/JP2015/063846 filed May 14, 2015.
Hanan S. Samaha, et al., "Modulation of Apoptosis by Sulindac, Curcumin, Phenylethyl-3-methylcaffeate, and 6-Phenylhexyl Isothiocyanate: Apoptotic Index as a Biomarker in Colon Cancer Chemoprevention and Promotion", Cancer Research, Apr. 1, 1997, vol. 57, pp. 1301-1305.
Mou-Tuan Huang, et al., "Inhibitory Effects of Dietary Curcumin on Forestomach, Duodenal, and Colon Carcinogenesis in Mice", Cancer Research, Nov. 15, 1994, vol. 54, pp. 5841-5847.
Sreejayan, et al., "Curcuminoids as Potent Inhibitors of Lipid Peroxidation", J. Pharm. Pharmacol., 1994, vol. 46, pp. 1013-1016.
R. C. Srimal, et al., "Pharmacology of diferuloyl methane (curcumin), a non-steroidal anti-inflammatory agent", J. Pharm. Pharmac., 1973, vol. 25, pp. 447-452.
D. Subba Rao, et al., "Effect of Curcumin on Serum and Liver Cholesterol Levels in the Rat", J. Nutrition, 1970, vol. 100, pp. 1307-1315.
P. Suresh Babu, et al., "Hypolipidemic action of curcumin, the active principle of turmeric (*Curcuma longa*) in streptozotocin induced diabetic rats", Molecular and Cellular Biochemistry, 1997, vol. 166, pp. 169-175.

(Continued)

*Primary Examiner* — Yih-Horng Shiao
(74) *Attorney, Agent, or Firm* — Oblon, McClelland, Maier & Neustadt, L.L.P.

(57) ABSTRACT

Provided is a composition for oral intake, which exhibits improved oral absorbability of curcumin and/or an analog thereof and can be produced conveniently and inexpensively. A complex of curcumin and/or an analog thereof and a water-soluble cellulose derivative is disclosed.

11 Claims, 12 Drawing Sheets

(56) References Cited

OTHER PUBLICATIONS

Shingo Yano, et al., "Antiallergic Activity of Curcuma longa (II) Features of inhibitory actions of histamine release from mast cells", Natural Medicines, 2000, vol. 54, No. 6, pp. 325-329.
Pamela Maher, et al., "A pyrazole derivative of curcumin enhances memory", Neurobiology of Aging, 2010, vol. 31, pp. 706-709.
Tatsuya Morimoto, et al., "The dietary compound curcumin inhibits p300 histone acetyltransferase activity and prevents heart failure in rats", The Journal of Clinical Investigation, Mar. 2008, vol. 118, No. 3, pp. 868-878.
Ajay Kumar Sav, et al., "Preparation of curcumin solid dispersions using hydrophilic polymers by different techniques and in vitro characterization", Asian Journal of Pharmaceutical Sciences, 2012, vol. 7, No. 4, pp. 271-279.
Satomi Onoue, et al. "Formulations Design and Photochemical Studies on Nanocrystal Solid Dispersion of Curcumin With Improved Oral Bioavailability", Journal of Pharmaceutical Sciences, Apr. 2010, vol. 99, No. 4, pp. 1871-1881.
Bin Li, et al., "Both solubility and chemical stability of curcumin are enhanced by solid dispersion in cellulose derivative matrices", Carohydrate Polymers, Oct. 15, 2013, vol. 98, Issue 1, 11 pages.
Lindsay A. Weiel, et al., "Curcumin amorphous solid dispersions: the influence of intra and intermolecular bonding on physical stability", Phamaceutical Development and Technology, vol. 19, No. 8, 2014, pp. 976-986.

Modern Pharmaceutics, Edited by Akira Tsuji, a professor of Kanazawa University, Nov. 1, 2015, Nankodo Co., Ltd., p. 97 (w/partial English translation).
Pharmaceutical Experimental Method, The Must-Have Manual for Pharmaceutical Scientist, vol. 1, Physical Pharmacy, Edited by The Academy of Pharmaceutical Science and Technology, Japan, Issued by Nankodo Co., Ltd., dated Apr. 5, 2014 (with partial English translation).
Etsuo Yonemochi, "Physicochemical Properties for Amorphous Pharmaceuticals and their Stability", Cryobiology and Cryotechnology, Japanese Society for Cryobiology and Cryotechnology, vol. 51, No. 51, pp. 25-30, 2005 (with partial English translation).
Satomi Onoue, et al., "Improvement in absorbability of poorly absorbable and development of novel dosing preparation", Improvement of Gastrointestinal and Transmucosal Absorption of Poorly Absorbable Drugs and Development of Novel dosage Forms of These Drugs, dated Apr. 2, 2012, Issuer: Kenji Tsuji, Publisher: CMC Publishing Co., LTD., 34-40 (with partial English translation).
Notification dated Sep. 25, 2018 w/ submission filed on Sep. 3, 2018 by a anonymous third party in JP Application No. 2016-519297 (Notification 1).
Notification dated Sep. 25, 2018 w/ submission filed on Aug. 29, 208 by a anonymous third party in JP Application No. 2016-519297 (Notification 2).

* cited by examiner

[Fig. 1]
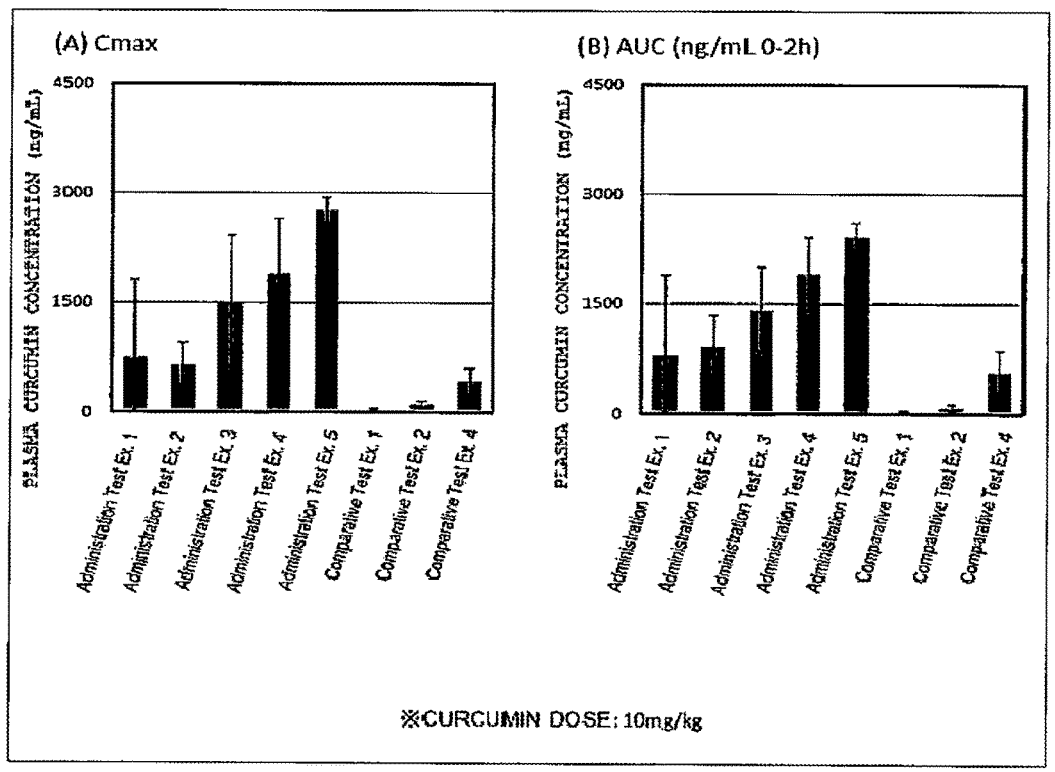

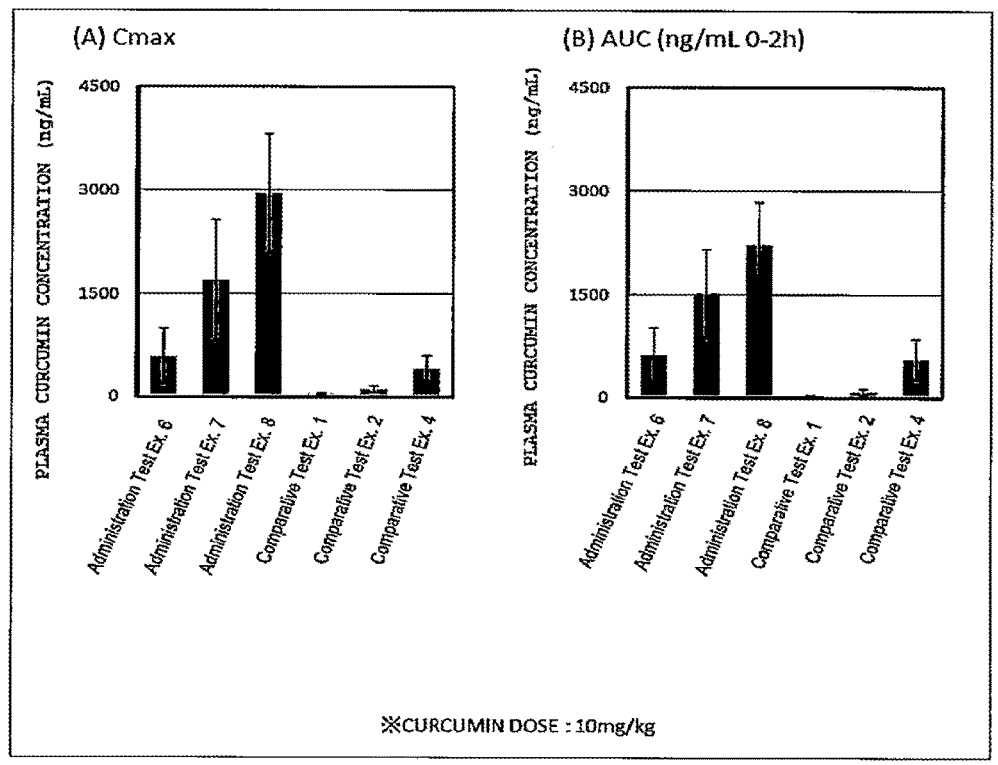
[FIG. 2]

[Fig. 3]
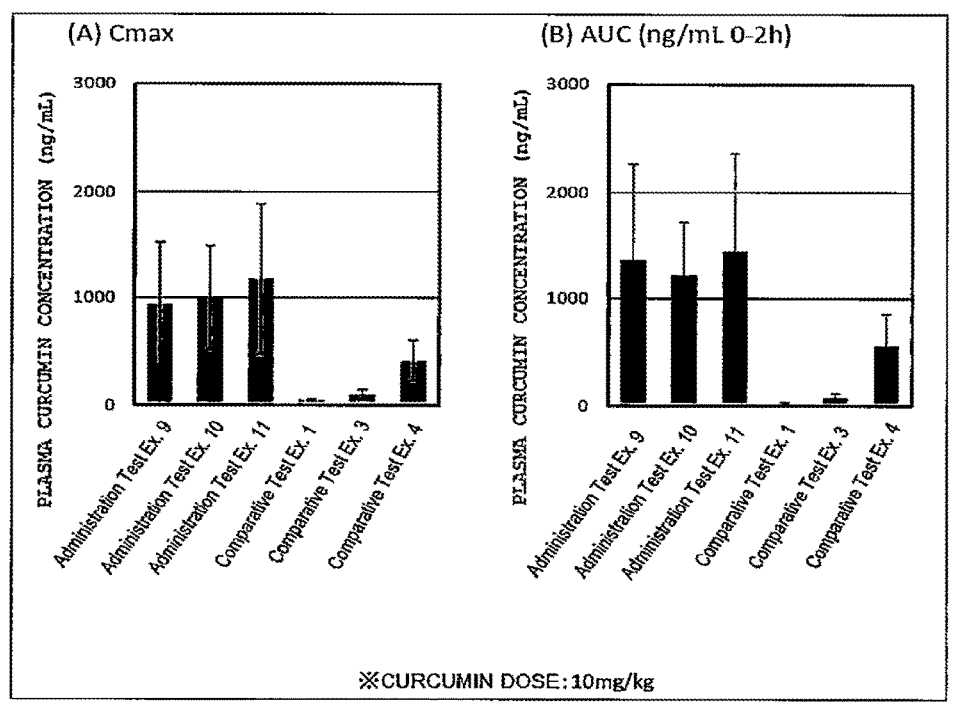

[Fig. 4]
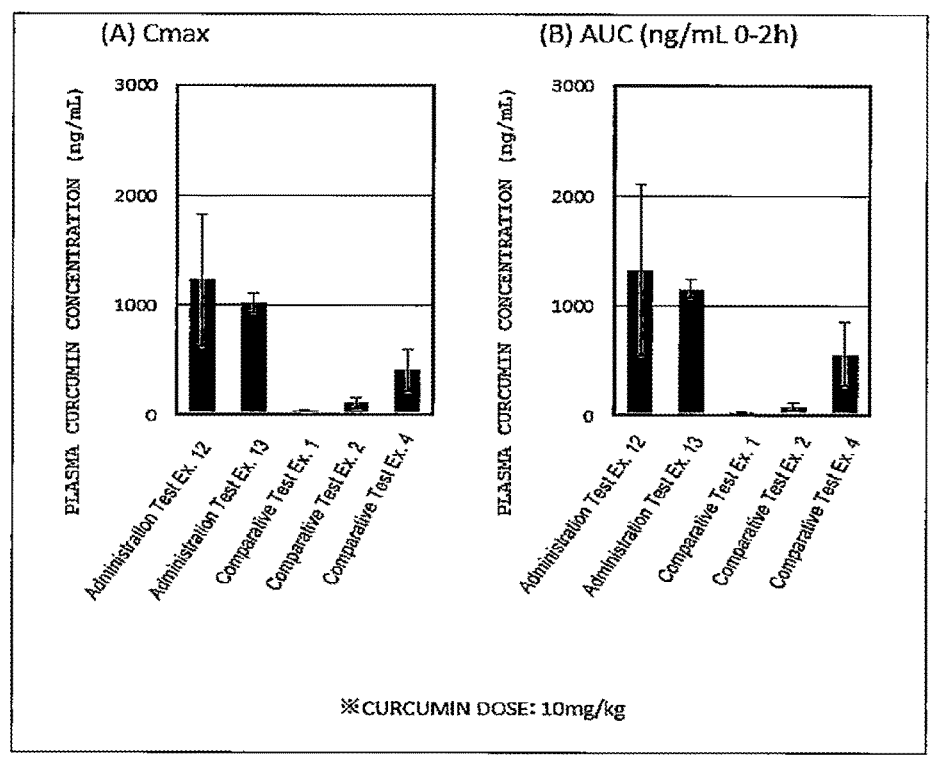

[Fig. 5]
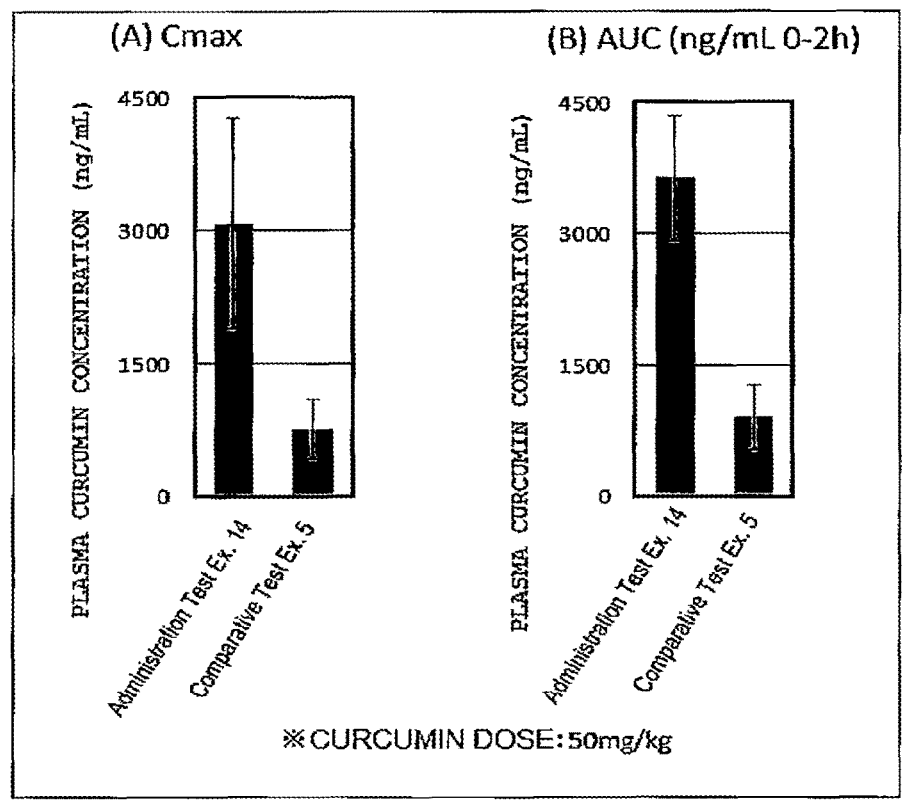

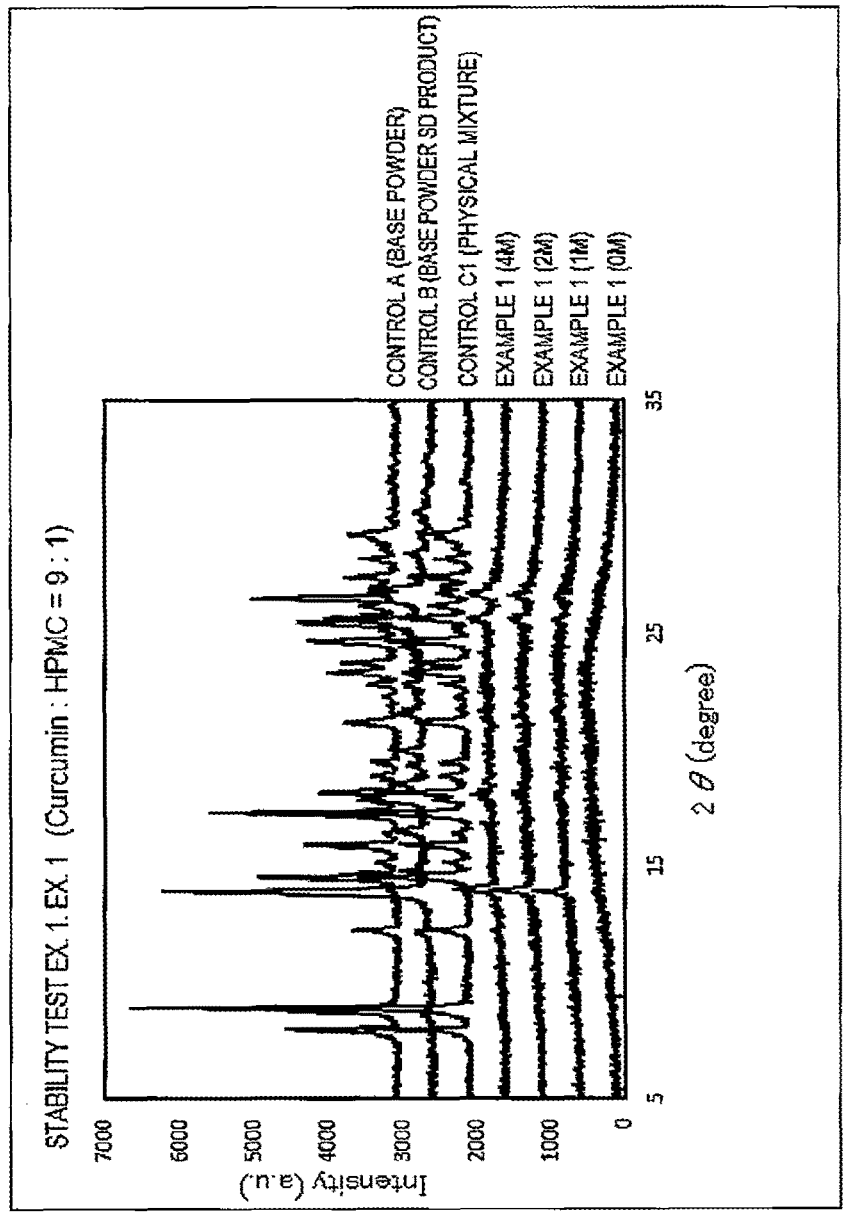
[Fig. 6]

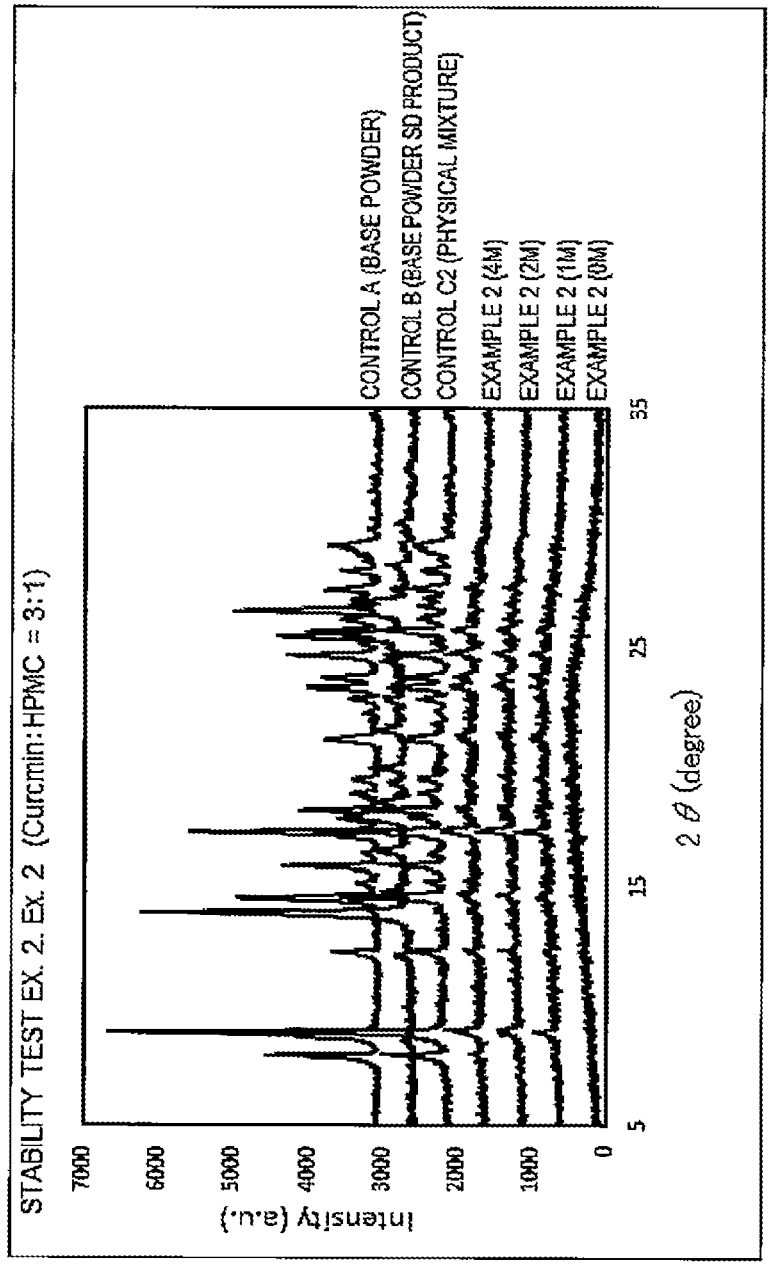
[Fig. 7]

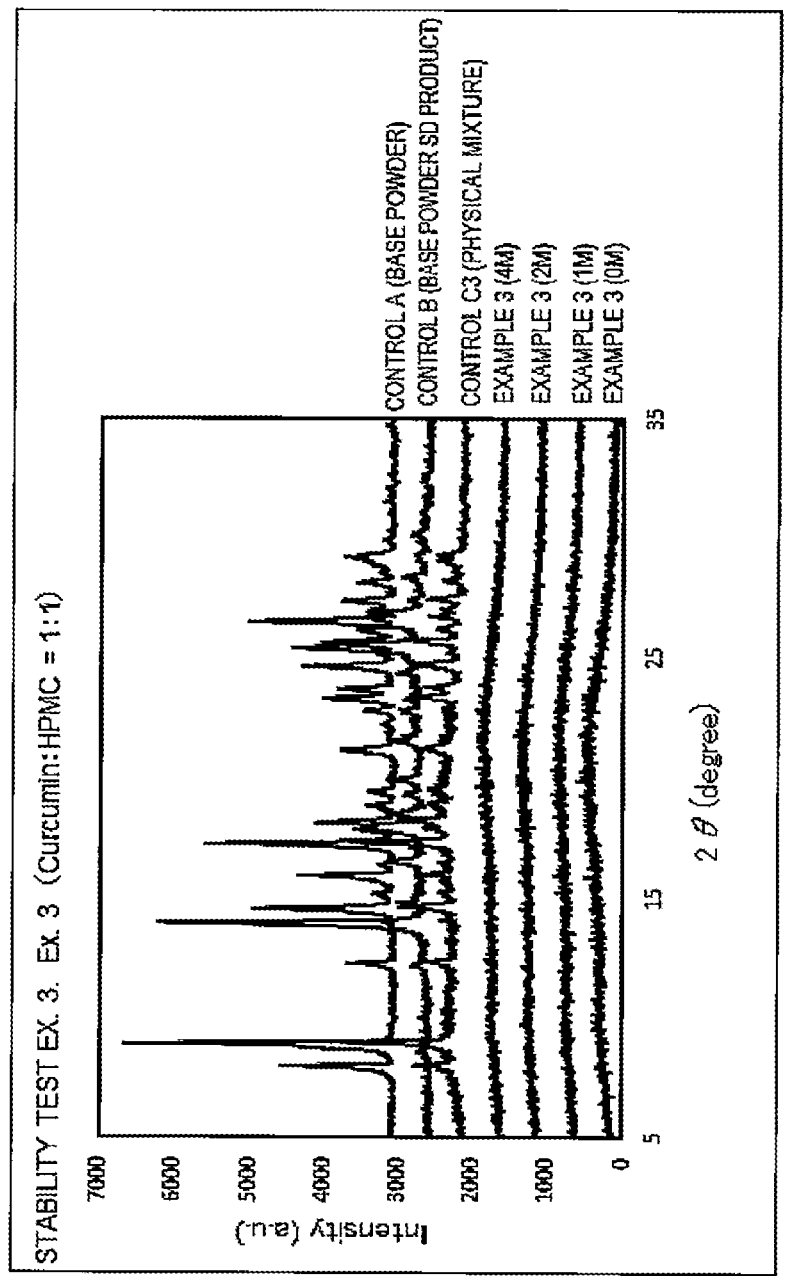

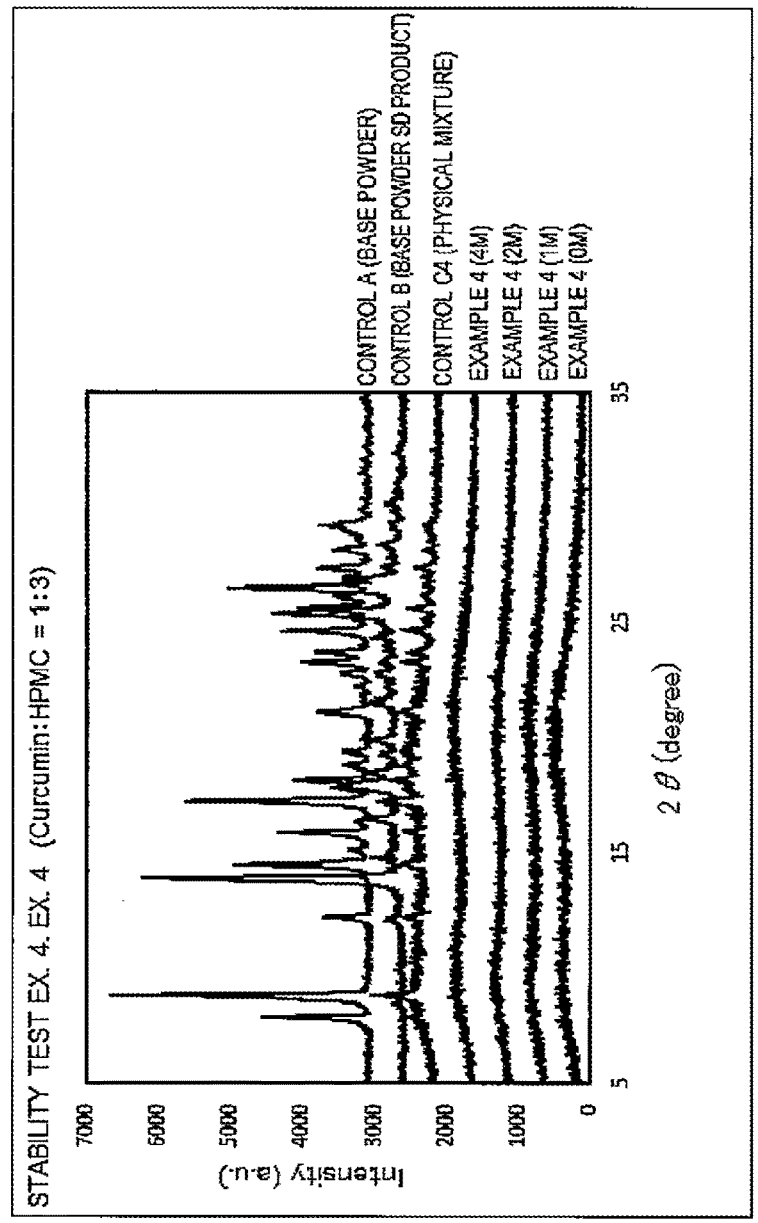

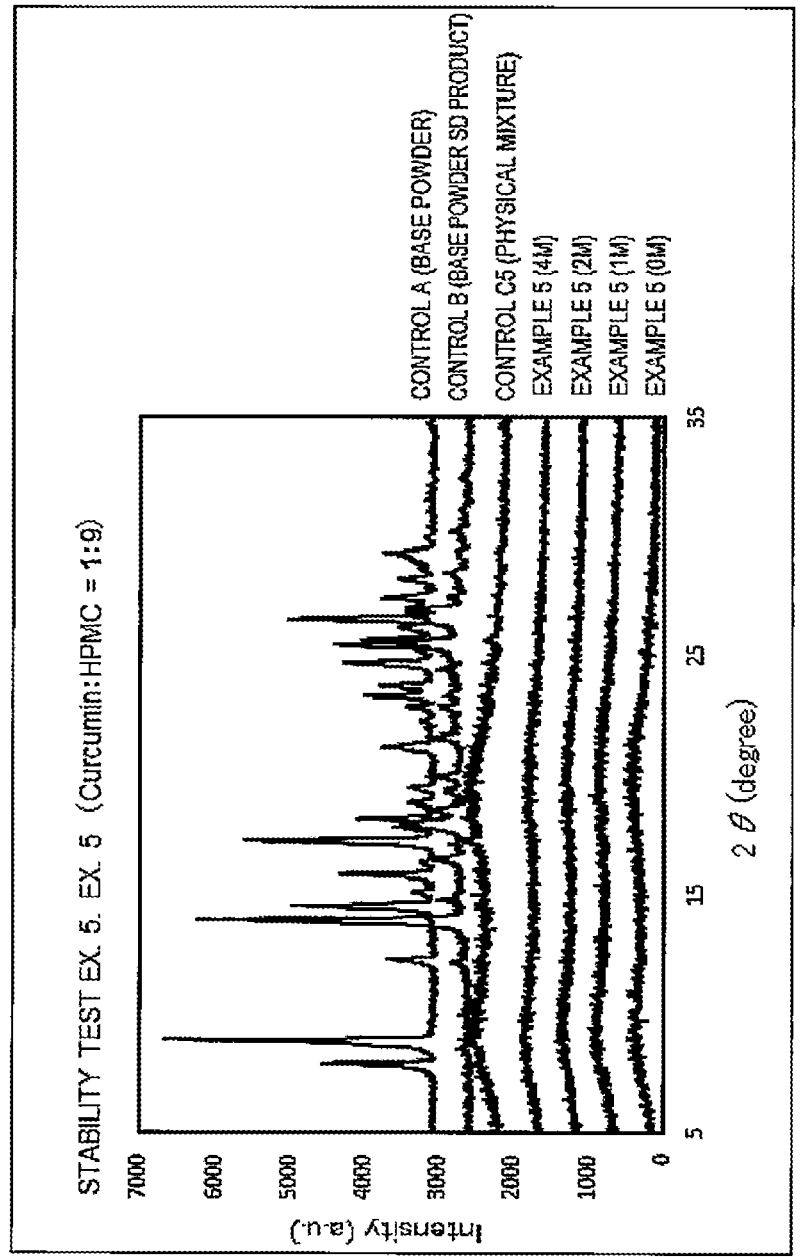
[Fig. 10]

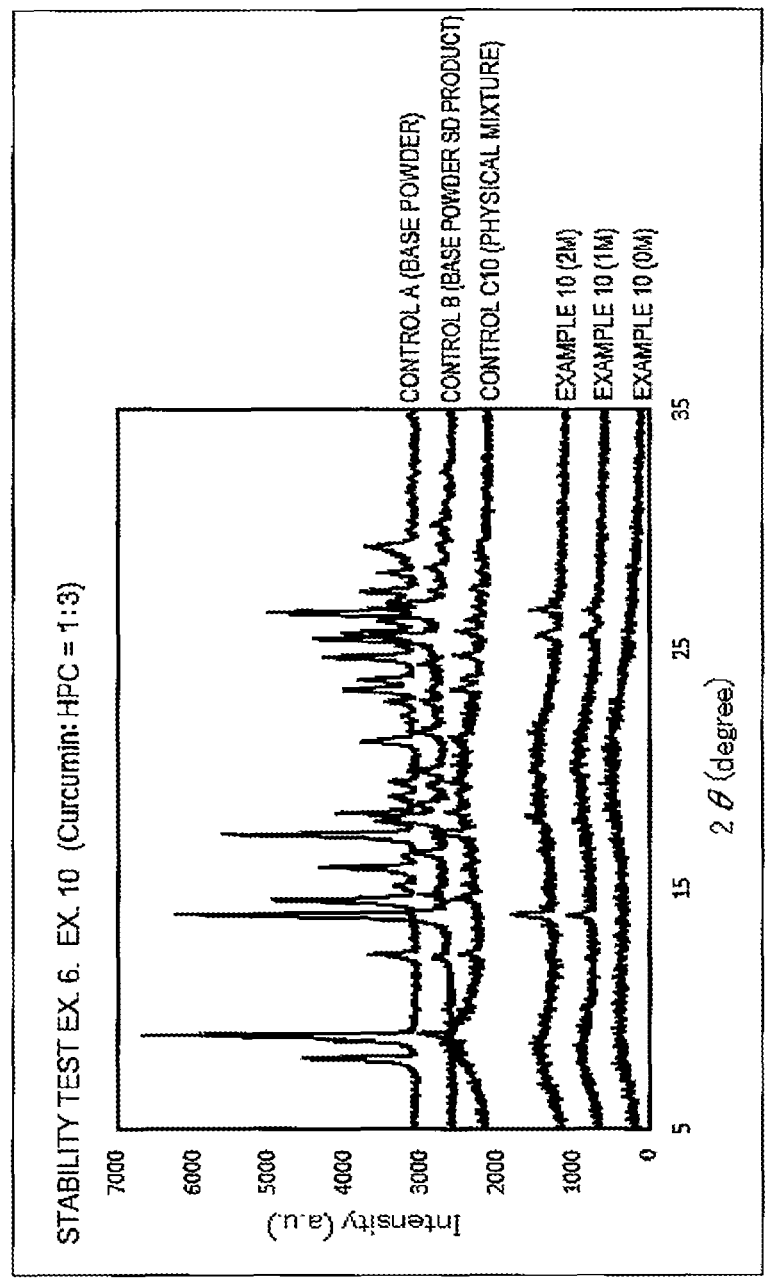

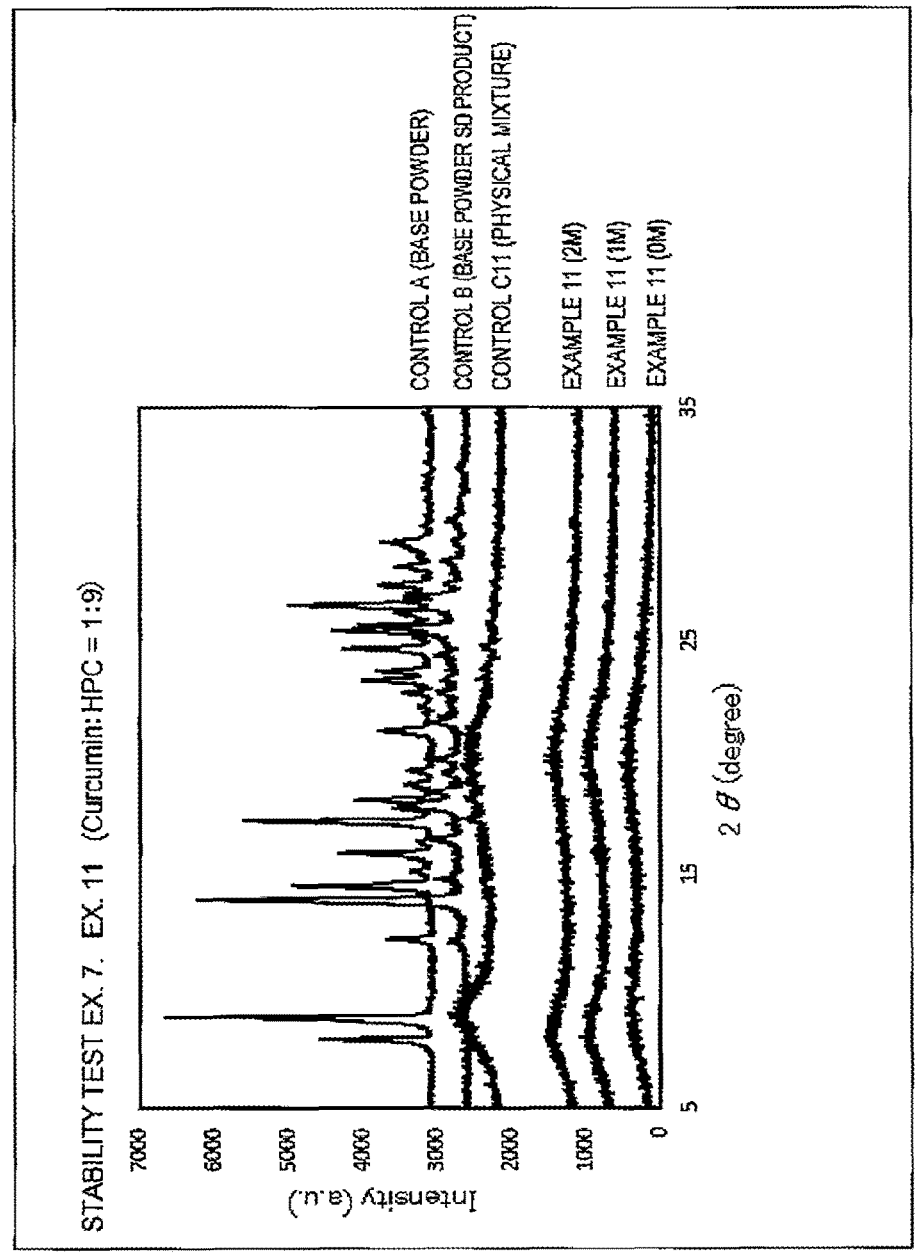

COMPOSITION FOR ORAL INTAKE

FIELD OF THE INVENTION

The present invention relates to a composition for oral intake comprising curcumin and/or an analog thereof.

BACKGROUND OF THE INVENTION

Curcumin is one of curcuminoids, which are main components of turmeric dyes that are obtainable from the roots and rhizomes of turmeric. Curcuminoids have been traditionally known as cholagogues, and it is also known that curcuminoids have, for example, tumorigenesis inhibitory effect, antioxidant effect, anti-inflammatory effect, hypocholesterolemic effect, anti-allergic effect, cerebral disease prophylactic effect, and cardiac disease prophylactic and therapeutic effects (Patent Literatures 1 and 2, and Non Patent Literatures 1 to 9). Since curcumin has such physiological activities, application of curcumin in, for example, pharmaceuticals, cosmetics, and nutritional supplementary foods has been considered.

However, curcumin has a problem that curcumin has low solubility in water and exhibits a low absorption rate when orally ingested. It has been reported that when a micronized curcuminoid is combined with gum ghatti in order to address the problem, oral absorbability is enhanced (Patent Literature 3).

Furthermore, it has also been reported that, for the purpose of improving photostability and coloring power of curcumin, a complex of curcumin with, for example, a water-soluble, branched or cyclic polysaccharide or a protein may be formed (Patent Literature 4).

CITATION LIST

Patent Literatures

Patent Literature 1: JP 2005-41817 A
Patent Literature 2: JP 2010-260816 A
Patent Literature 3: JP 2009-263638 A
Patent Literature 4: JP 3-97761 A

Non Patent Literatures

Non Patent Literature 1: Samaha H S, Kelloff G J, Steele V, Rao C V, Reddy B S., Cancer Res., 57, 1301-5 (1997)
Non Patent Literature 2: Huang M T, Lou Y R, Ma W, Newmark H L, Reuhl K R, Conney A H., Cancer Res., 54, 5841-7 (1994)
Non Patent Literature 3: Sreejayan, Rao M N., J Pharm Pharmacol., 46, 1013-6 (1994)
Non Patent Literature 4: Srimal R C, Dhawan B N., J Pharm Pharmacol., 25, 447-52 (1973)
Non Patent Literature 5: Rao D S, Sekhara N C, Satyanarayana M N, Srinivasan M., J Nutr., 100, 1307-16 (1970)
Non Patent Literature 6: Babu P S, Srinivasan K., Mol Cell Biochem., 166, 169-75 (1997)
Non Patent Literature 7: Yano S, Terai M, Shimizu K L, Futagami Y, Horie S., Natural Medicines, 54, 325-9 (2000)
Non Patent Literature 8: Maher P, Akaishi T, Schubert D, Abe K., Neurobiol Aging., July 16. [Equb ahead of print] (2008)
Non Patent Literature 9: Morimoto T, Sunagawa Y, Kawamura T, Takaya T, Wada H, Nagasawa A, Komeda M, Fujita M, Shimatsu A, Kita T, Hasegawa K. J Clin Invest., 118, 868-878 (2008)

SUMMARY OF THE INVENTION

Technical Problem

Several curcumin compositions exhibiting enhanced absorbability of curcumin into the body upon oral intake have been developed hitherto; however, the absorbability into the body upon oral intake still cannot be said to be sufficient, and also, in order to produce those compositions, special technologies or complicated operations are needed. Therefore, there is a demand for the development of a method for producing compositions comprising curcumin and analogs thereof, which exhibit superior oral absorbability, conveniently and inexpensively.

On the other hand, in regard to the curcumin complex described in Patent Literature 4, the relevant complex is to be utilized as a colorant for foods, and nothing is discussed in connection with the enhancement of the absorbability of curcumin and/or an analog thereof into the body.

Therefore, the present invention relates to provision of a composition for oral intake, which exhibits improved oral absorbability of curcumin and/or an analog thereof and can be produced conveniently and inexpensively.

Solution to Problem

Thus, the inventors of the present invention examined oral absorbability of mixtures of curcumin and/or an analog thereof with various components, and processed products of the mixtures, and the inventors found that a complex formed from curcumin and/or an analog thereof and a water-soluble cellulose derivative by an easy operation exhibits markedly enhanced oral absorbability compared to a mixture thereof, and that a composition comprising this complex is useful as a composition for oral intake for securely exhibiting various physiological effects of curcumin and/or an analog thereof. Thus, the inventors completed the present invention.

That is, the present invention provides the following items [1] to [9].

[1] A complex comprising curcumin and/or an analog thereof and a water-soluble cellulose derivative.
[2] The complex according to [1], wherein curcumin and/or the analog thereof comprises curcumin or a turmeric dye.
[3] The complex according to [1] or [2], wherein the water-soluble cellulose derivative is a component selected from the group consisting of methyl cellulose, ethyl cellulose, hydroxypropyl cellulose, hydroxypropylmethyl cellulose, carboxymethyl cellulose, and a carboxymethyl cellulose salt.
[4] The complex according to any one of [1] to [3], wherein a content ratio (A/B) between (A) curcumin and/or the analog thereof, and (B) the water-soluble cellulose derivative is 0.02 to 10.
[5] The complex according to any one of [1] to [4], wherein the complex is obtainable by removing a solvent from water-organic solvent mixed solution containing curcumin and/or the analog thereof and the water-soluble cellulose derivative.
[6] The complex according to any one of [1] to [5], wherein curcumin and/or the analog thereof is amorphous.
[7] A composition for oral intake, comprising the complex according to any one of [1] to [6].

[8] A method for producing a complex of curcumin and/or an analog thereof and a water-soluble cellulose derivative, the method comprising a step of dissolving curcumin and/or an analog thereof and a water-soluble cellulose derivative in a water-organic solvent mixed solvent; and a step of removing water and the organic solvent from the solution.

[9] A method for producing a complex of curcumin and/or an analog thereof and a water-soluble cellulose derivative, the method comprising a step of dissolving curcumin and/or an analog thereof in an organic solvent; a step of dissolving a water-soluble cellulose derivative in water; a step of mixing the organic solvent solution containing curcumin and/or the analog thereof, with the aqueous solution containing the water-soluble cellulose derivative; and a step of removing water and the organic solvent from the mixed solution.

Effects of Invention

The complex of curcumin and/or an analog thereof and a water-soluble cellulose derivative of the present invention is easily formed from a water-organic solvent mixed solution containing the two components, and the oral absorbability of curcumin and/or an analog thereof at the time of orally ingesting a composition comprising this complex is markedly superior to the case in which a mixture of those components is orally ingested. Therefore, composition for oral intake comprising the complex of the present invention is useful as, for example, pharmaceutical, cosmetic, nutritional supplementary food, or functional food, all of which are capable of exhibiting the physiological effects of curcumin and/or an analog thereof.

BRIEF DESCRIPTION OF DRAWINGS

FIG. 1 shows Cmax (ng/mL) and AUC (ng/mL·0 to 2 h) in the case of a curcumin dose of 10 mg/kg.

FIG. 2 shows Cmax (ng/mL) and AUC (ng/mL·0 to 2 h) in the case of a curcumin dose of 10 mg/kg.

FIG. 3 shows Cmax (ng/mL) and AUC (ng/mL·0 to 2 h) in the case of a curcumin dose of 10 mg/kg.

FIG. 4 shows Cmax (ng/mL) and AUC (ng/mL·0 to 2 h) in the case of a curcumin dose of 10 mg/kg.

FIG. 5 shows Cmax (ng/mL) and AUC (ng/mL·0 to 2 h) in the case of a curcumin dose of 50 mg/kg.

FIG. 6 shows the results of X-ray diffraction of a curcumin-hydroxypropylmethyl cellulose (9:1) complex powder.

FIG. 7 shows the results of X-ray diffraction of a curcumin-hydroxypropylmethyl cellulose (3:1) complex powder.

FIG. 8 shows the results of X-ray diffraction of a curcumin-hydroxypropylmethyl cellulose (1:1) complex powder.

FIG. 9 shows the results of X-ray diffraction of a curcumin-hydroxypropylmethyl cellulose (1:3) complex powder.

FIG. 10 shows the results of X-ray diffraction of a curcumin-hydroxypropylmethyl cellulose (1:9) complex powder.

FIG. 11 shows the results of X-ray diffraction of a curcumin-hydroxypropyl cellulose (1:3) complex powder.

FIG. 12 shows the results of X-ray diffraction of a curcumin-hydroxypropyl cellulose (1:9) complex powder.

DESCRIPTION OF EMBODIMENTS

The complex of the present invention is a complex of (A) curcumin and/or an analog thereof, and (B) a water-soluble cellulose derivative.

(A) curcumin is a main component of curcuminoids that are included in turmeric dyes, and is a compound represented by the following structural formula (1):

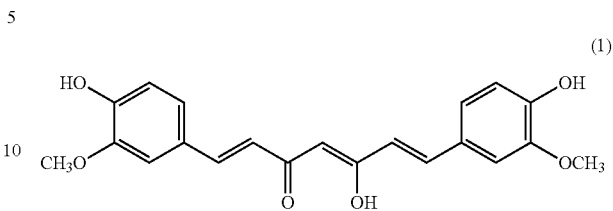

In regard to the curcumin according to the present invention, a chemically synthesized curcumin may be used, or a commercially distributed product as a turmeric dye may also be used. Examples of the turmeric dye include turmeric powder that is obtained by processing a dried product of the roots and rhizomes of Curcuma longa LINNE into powder; crude curcumin or oleoresin (turmeric oleoresin) obtainable by extracting the turmeric powder using an appropriate solvent (for example, ethanol, oils and fats, propylene glycol, hexane, or acetone); and purified curcumin.

Meanwhile, curcumin includes both keto-form and enol-form, which are tautomers.

Examples of the curcumin analog include demethoxycurcumin, bisdemethoxycurcumin, tetrahydrocurcumin, and dihydroxytetrahydrocurcumin. Meanwhile, turmeric dyes include curcumin, demethoxycurcumin, and bisdemethoxycurcumin.

Examples of the (B) water-soluble cellulose derivative include an etherified cellulose in which a portion of the hydroxyl groups of glucose that constitutes cellulose have been etherified, and specific examples thereof include methyl cellulose, ethyl cellulose, hydroxypropyl cellulose, hydroxypropylmethyl cellulose, carboxymethyl cellulose, and a carboxymethyl cellulose salt. Here, examples of the carboxymethyl cellulose salt include carboxymethyl cellulose alkali metal salts such as carboxymethyl cellulose sodium; and carboxymethyl cellulose alkaline earth metal salts such as carboxymethyl cellulose calcium.

Among these water-soluble cellulose derivatives, hydroxypropyl cellulose and hydroxypropylmethyl cellulose are more preferred, and hydroxypropylmethyl cellulose is even more preferred.

The content ratio (A/B) between (A) curcumin and/or an analog thereof and the (B) water-soluble cellulose derivative in the complex of the present invention is preferably 0.02 to 10, more preferably 0.03 to 10, even more preferably 0.05 to 10, still more preferably 0.1 to 10, even more preferably 0.1 to 5, and still more preferably 0.1 to 3, from the viewpoint of obtaining excellent oral absorbability and from the viewpoint of size reduction of the preparation.

The complex of the present invention refers to a product formed as a result of an interaction (for example, hydrogen bonding, hydrophobic bonding, or intermolecular force such as van der Waals force) between curcumin and/or an analog thereof and a water-soluble cellulose derivative. Meanwhile, although the structure of the complex of the present invention is not clearly known, as will be disclosed in the Examples described below, since the oral absorbability is remarkably enhanced compared to a mixture of the component (A) and the component (B), it is obvious that the component (A) and the component (B) have formed a certain complex. Curcumin and analogs thereof are almost insoluble in water and are soluble in organic solvents. On the other hand, the water-soluble cellulose derivative is highly soluble in water. It is preferable that the complex of the present invention is a product obtainable by removing the solvent from water-organic solvent mixed solution containing curcumin and/or an analog thereof and a water-soluble cellulose derivative. It is speculated that as the two components, curcumin and/or an analog thereof and the water-soluble cellulose derivative, are once dissolved in a water-organic mixed solvent, a complex such as, for example, an associate of the two components, is formed.

The complex of the present invention is produced by, for example, a method including a step of dissolving (A) curcumin and/or an analog thereof and (B) a water-soluble cellulose derivative in a water-organic solvent mixed solvent; and a step of removing water and the organic solvent from the solution.

More specifically, the complex of the present invention is produced by a method including a step of dissolving (A) curcumin and/or an analog thereof in an organic solvent; a step of dissolving (B) a water-soluble cellulose derivative in water; a step of mixing the organic solvent solution containing curcumin and/or an analog thereof, with the aqueous solution containing the water-soluble cellulose derivative; and a step of removing water and the organic solvent from the relevant mixed solution.

Examples of the organic solvent for dissolving (A) curcumin and/or an analog thereof include hydrophilic organic solvents, for example, a $C_2$-$C_6$ alcohol such as ethanol or isopropanol; and a $C_2$-$C_6$ glycol such as propylene glycol. Among them, a $C_2$-$C_6$ alcohol is preferred, and ethanol is more preferred. The amount of use of the relevant organic solvent may be any amount capable of dissolving curcumin and/or an analog thereof. Furthermore, the amount of use of water for dissolving the water-soluble cellulose derivative may be any amount capable of dissolving the water-soluble cellulose derivative.

It is preferable that mixing of the organic solvent solution containing (A) curcumin and/or an analog thereof with the aqueous solution containing the (B) water-soluble cellulose derivative is performed such that the ratio A/B described above becomes 0.02 to 10.

Examples of the means for removing water and the organic solvent from the mixed solution thus obtained include drying by evaporation, drying under reduced pressure, spray drying, freeze-drying, warm air drying, cold air drying, and air drying; however, drying under reduced pressure and spray drying are preferred.

The complex of the present invention exhibits satisfactory oral absorbability of curcumin and/or an analog thereof, and that oral absorbability is markedly superior to the oral absorbability of a mixture of curcumin and/or an analog thereof and the water-soluble cellulose derivative. Therefore, a composition for oral intake comprising the relevant complex is useful as pharmaceutical, cosmetic, nutritional supplementary food, functional food, or food for specified health use, all of which are intended to have the physiological activity of curcumin and/or an analog thereof exhibited by oral administration.

Furthermore, the content of the complex in the composition for oral intake related to the present invention is preferably 10% by mass or more, 15% by mass or more, and more preferably 30% by mass or more, from the viewpoints of reduction of a single dose, taste, and oral absorbability. Furthermore, the content of the complex is preferably 80% by mass or less, more preferably 70% by mass or less, and even more preferably 60% by mass or less. Specifically, the content is preferably 10% to 80% by mass, more preferably 15% to 80% by mass, even more preferably 30% to 70% by mass, and still more preferably 30% to 60% by mass.

Specific examples of the pharmaceutical, cosmetic, nutritional supplementary food, functional food, and food for specified health use according to the present invention include beverages such as refreshing beverages, carbonated beverages, nutritional beverages, fruit beverages, and sour milk beverages; frozen desserts such as ice cream, ice sherbet, and snow cones; confectionaries such as lollipops, candies, chewing gums, chocolates, tablet candies, snacks, biscuits, jellies, jam, cream, and baked confectioneries; dairy products such as processed milk and fermented milk; condiments such as sauces and gravies; soups, stews, salads, everyday dishes, rice seasonings, pickled vegetables; other various forms of health/nutritional supplementary foods; pharmaceuticals such as tablets, capsules, drinks, and troches; and quasi-drugs. The additives that are conventionally used for producing these can be used.

Examples of the additives described above include glucose, fructose, sucrose, maltose, sorbitol, stevioside, rubusoside, corn syrup, lactose, mannite, dextrin, citric acid, sodium citrate, tartaric acid, malic acid, succinic acid, lactic acid, L-ascorbic acid, dl-α-tocopherol, sodium erythorbate, glycerin, propylene glycol, gum arabic, carrageenan, casein, gelatin, pectin, agar-agar, vitamin C, vitamin B's, vitamin E, nicotinic acid amide, calcium pantothenate, amino acids, calcium salt, *stevia*, enzyme-treated *stevia*, dyes, fragrances, and preservatives.

Furthermore, examples of the form of the composition for oral intake of the present invention include tablets, capsules, granules, fine granules, powders, and syrup preparations. In order to formulate these preparations, for example, excipients, binders, disintegrants, lubricating agents, and coating agents can be used.

The daily dose of the composition for oral intake of the present invention is preferably from 0.03 g to 12 g, which amount has been generally recognized to be safe as a conventional amount of curcumin for an adult.

EXAMPLES

Next, the present invention will be explained in more detail by way of Examples.

Examples 1 to 13

(Production of Various Complexes)

Examples 1 to 5 and 9 to 13

(Production Method A: Drying Using Spray Dryer)

Solution containing a curcumin-hydroxypropylmethyl cellulose complex or curcumin-hydroxypropyl cellulose complex was prepared by adding 1.10 g to 8.77 g (1.0 g to 8.0 g in terms of the amount of curcumin) of turmeric extract powder (Lot. NCTH0012012) having a curcumin content of 91.2% (w/w), which was donated by San-Ei Gen F.F.I., Inc., and 0.2 g to 64.8 g of hydroxypropylmethyl cellulose (HPMC; METOLOSE SE-06 or SE-03, manufactured by Shin-Etsu Chemical Co., Ltd.) or hydroxypropyl cellulose (HPC; SSL, manufactured by Nippon Soda Co., Ltd.) to 400 mL of 70% or 80% (v/v) ethanol solution, and stirring the mixture while heating the mixture to about 80° C.

Furthermore, dextrin as an additive was added to and dissolved in the curcumin-hydroxypropylmethyl cellulose complex-containing solution, and thereby, a curcumin-hydroxypropylmethyl cellulose complex including dextrin was produced.

Next, this solution was spray dried using a $N_2$ gas sealed circulation type spray system binary fluid nozzle type spray dryer (PULVIS MINI-SPRAY GS-31, manufactured by Yamato Scientific Co., Ltd.), under the conditions of an inlet temperature of 140° C., an outlet temperature of 80° C. to 90° C., a spray pressure of 0.10 MPa to 0.13 MPa, a feed rate of 10 mL/min, and an orifice pressure of 75 mmHg, and thus, a curcumin-hydroxypropymethyl cellulose complex or curcumin-hydroxypropyl cellulose complex was produced.

Examples 6 to 8

(Production Method B: Drying Using Evaporator)

Solution containing a curcumin-hydroxypropylmethyl cellulose complex was prepared by adding 1.10 g or 2.19 g (1.0 g or about 2.0 g in terms of the amount of curcumin) of turmeric extract powder (Lot. NCTH0012012) having a curcumin content of 91.20 (w/w), which was donated by San-Ei Gen F.F.I., Inc., and 0.2 g, 4 g, 6 g, or 10 g of hydroxypropylmethyl cellulose (HPMC; METOLOSE SE-06, manufactured by Shin-Etsu Chemical Co., Ltd.) to 200 mL or 400 mL of a 70% (v/v) ethanol solution, and stirring the mixture while heating the mixture to about 80° C.

Next, the solution was introduced into an evaporator (rotary evaporator N-1000, manufactured by Tokyo Rikakikai Co., Ltd.), and the solvent was distilled off by maintaining this solution at 80° C. under reduced pressure to solid-dry the solution. Thus, a dried product was collected. Furthermore, the dried product was introduced into a mortar and pulverized with a pestle, and thereby, a curcumin-hydroxypropylmethyl cellulose complex was produced.

The compositions of the complexes obtained in Examples 1 to 13 are presented in Table 1.

TABLE 1

| | Curcumin:water-soluble cellulose derivative | Water-soluble cellulose derivative used | Presence or absence of additive | Production method | Solvent used (mL) | Curcumin (g) | Water-soluble cellulose derivative (g) | Additive (g) |
|---|---|---|---|---|---|---|---|---|
| Example 1 | 9:1 | HPMC SE-06 | Absent | A | 80% (v/v) ethanol solution 400 | 7.2 | 0.8 | 0 |
| Example 2 | 3:1 | HPMC SE-06 | Absent | A | 80% (v/v) ethanol solution 400 | 6.0 | 2.0 | 0 |
| Example 3 | 1:1 | HPMC SE-06 | Absent | A | 80% (v/v) ethanol solution 400 | 8.0 | 8.0 | 0 |
| Example 4 | 1:3 | HPMC SE-06 | Absent | A | 70% (v/v) ethanol solution 400 | 6.0 | 18.0 | 0 |
| Example 5 | 1:9 | HPMC SE-06 | Absent | A | 70% (v/v) ethanol solution 400 | 4.0 | 36.0 | 0 |
| Example 6 | 10:1 | HPMC SE-06 | Absent | B | 70% (v/v) ethanol solution 400 | 2.0 | 0.2 | 0 |
| Example 7 | 1:3 | HPMC SE-06 | Absent | B | 70% (v/v) ethanol solution 400 | 2.0 | 6.0 | 0 |
| Example 8 | 1:10 | HPMC SE-06 | Absent | B | 70% (v/v) ethanol solution 200 | 1.0 | 10.0 | 0 |
| Example 9 | 1:2 | HPC SSL | Absent | A | 80% (v/v) ethanol solution 400 | 8.0 | 16.0 | 0 |
| Example 10 | 1:3 | HPC SSL | Absent | A | 80% (v/v) ethanol solution 400 | 8.0 | 24.0 | 0 |
| Example 11 | 1:9 | HPC SSL | Absent | A | 80% (v/v) ethanol solution 400 | 7.2 | 64.8 | 0 |
| Example 12 | 1:1 | HPMC SE-06 | Present (Dextrin) | A | 70% (v/v) ethanol solution 400 | 6.0 | 6.0 | 24.0 |
| Example 13 | 1:1 | HPMC SE-03 | Present (Dextrin) | A | 70% (v/v) ethanol solution 400 | 6.0 | 6.0 | 24.0 |

Test Example 1

(Oral Absorbability of Various Complexes)

(1) Test Animal

For the test animal, 6-week old SD rats (male, body weight: 170 g to 260 g, Charles River Laboratories Japan, Inc.) were used.

(2) Administration Method

In regard to the administration method, the various complexes (Examples 1 to 13) produced as described above were each added to water for injection in a predetermined amount, subsequently the mixture was made up to 20 mL so as to obtain a curcumin concentration of 1 mg/mL, the mixture was mixed using an ultrasonic generator, and the mixture was forcibly orally administered to test animals (n 3 or 5) that had been fasted for 12 hours or longer before administration, using a feeding needle, such that the curcumin dose would be 10 mg/kg (Administration Test Examples 1 to 13) or 50 mg/kg (Administration Test Example 14).

Meanwhile, the cases of administering curcumin base powder (Comparative Test Example 1); physical mixture obtained by simply physically mixing curcumin base powder and hydroxypropylmethyl cellulose powder or hydroxypropyl cellulose powder (curcumin:HPMC=1:3 or curcumin HPC=1:3) (Comparative Test Examples 2 and 3); or CR-031P powder (manufactured by Theravalues Corp.), which is a turmeric dye composition obtained by combining micronized curcuminoid with gum ghatti (Comparative Test Examples 4 and 5) was designated as controls.

(3) Measurement of Curcumin Concentration in Blood Plasma

For the measurement of the concentration of curcumin and/or an analog thereof in blood plasma, measurement was made by the following method, using heparinized blood plasma obtained by collecting about 0.5 mL of blood from the jugular vein of the test animals without anesthesia, after 30 minutes, 1 hour, and 2 hours from the initiation of administration.

a. Preliminary treatment

100 μL of 0.1 M acetate buffer solution (pH 5.0) and 10 μL of β-glucuronidase solution (about 68,000 units/mL) were added to 20 μL of the collected blood plasma, and the mixture was maintained for 1 hour at 37° C. Subsequently, 10 μL of 50% (v/v) methanol including 20 ng/mL of mepronil, which was an internal standard liquid, and 0.5 mL of chloroform were added thereto, the mixture was stirred for 1 minute using a vortex mixer, and then the mixture was mixed for 15 minutes using an ultrasonic generator. An extraction-treated liquid thus prepared was separated into chloroform layer and an aqueous layer by centrifugation (13,000×g, for 5 minutes, at room temperature). This extraction treatment was repeated two times. Subsequently, the chloroform layer was collected, and the solvent was distilled off from this layer using a vacuum centrifugal concentrator to solid-dry the chloroform layer. 100 μL of 50% (v/v) methanol was added thereto, and then the mixture was centrifuged (13,000×g, for 5 minutes, at room temperature) to collect the supernatant.

b. Method for Measurement

2 μL of the supernatant produced as described above was subjected to an analysis using LC-MS/MS (manufactured by Shimadzu Corp.), and thereby the curcumin concentration in the blood plasma was measured. The conditions for the LC-MS/MS analysis were set such that the LC column was ATLANTIS T3 (2.1×150 mm, 3 μm, manufactured by Waters Corp.), the column temperature was 40° C., the flow rate was 0.2 mL/min, and the mobile phase included A: 0.1% aqueous solution of formic acid, and B: 0.1% formic acid/acetonitrile, and gradient elution was performed under the following conditions. Furthermore, the MS analysis conditions were set such that the ionization mode was Electron Spray thermo Ionization (ESI) mode, positive, and the measurement mode was Multiple Reaction Monitoring (MRM). The evaluation was performed under the conditions of curcumin 369.1→177.2 (m/z) and mepronil 270→119 (m/z).

On the other hand, production of a calibration curve used for quantitatively determine the amount of curcumin contained in a sample was carried out by making measurement using various standard solutions (curcumin concentration: 9 ng/mL to 225 ng/mL) prepared by adding 10 μL of 50% ethanol solution containing 20 ng/mL of mepronil to 90 μL of a 50% (v/v) methanol solution (curcumin standard liquid) containing 1.0, 2.0, 3.9, 7.8, 15.6, 31.3, 62.5, 125, or 250 ng/mL of curcumin, under the conditions similar to those described above.

TABLE 2

| * Conditions for gradient elution | | | | | |
|---|---|---|---|---|---|
| | Time (min) | | | | |
| | 0 | 1.8 | 7 | 7.01 | 15 |
| A (%) | 40 | 5 | 5 | 40 | 40 |
| B (%) | 60 | 95 | 95 | 60 | 60 |

(4) Results

The curcumin concentration in the blood plasma (ng/mL), the maximum blood concentration (Cmax (ng/mL)), and the area under the blood concentration-time curve (AUC (ng/mL·0 to 2 hr)) are presented in Tables 3 and 4 and FIGS. 1 to 5.

As is obvious from Tables 3 and 4 and FIGS. 1 to 5, the complexes of the present invention have markedly enhanced oral absorbability compared to the administration of curcumin alone and the administration of the mixture of curcumin and HPMC. Furthermore, even compared to the mixed micropulverization product of curcumin and gum ghatti (CR-031P), the complexes exhibited enhanced oral absorbability.

TABLE 3

| Case with curcumin dose: 10 mg/kg | | | | | | |
|---|---|---|---|---|---|---|
| Administered sample | | Curcumin concentration in blood plasma (ng/mL) | | | Cmax | AUC |
| | | 0.5 h | 1 h | 2 h | (ng/mL) | (ng/mL · 0-2 h) |
| Administration Test Example 1 (n = 3) | Example 1 | 132.2 ± 92.0 | 706.3 ± 1087.0 | 370.3 ± 556.6 | 739.8 ± 1060.6 | 780.9 ± 1098.9 |
| Administration Test Example 2 (n = 3) | Example 2 | 513.3 ± 322.8 | 649.7 ± 289.0 | 339.2 ± 113.1 | 649.7 ± 289.0 | 913.5 ± 412.1 |
| Administration Test Example 3 (n = 3) | Example 3 | 1463.8 ± 987.2 | 608.5 ± 251.4 | 436.7 ± 126.9 | 1518.6 ± 900.4 | 1406.6 ± 589.9 |
| Administration Test Example 4 (n = 3) | Example 4 | 1892.4 ± 762.4 | 958.1 ± 281.2 | 470.8 ± 47.1 | 1892.4 ± 762.4 | 1900.2 ± 506.2 |
| Administration Test Example 5 (n = 3) | Example 5 | 2759.2 ± 176.9 | 1077.9 ± 306.0 | 463.9 ± 64.9 | 2759.2 ± 176.9 | 2420.0 ± 197.6 |

TABLE 3-continued

Case with curcumin dose: 10 mg/kg

| | Administered sample | Curcumin concentration in blood plasma (ng/mL) | | | Cmax (ng/mL) | AUC (ng/mL · 0-2 h) |
|---|---|---|---|---|---|---|
| | | 0.5 h | 1 h | 2 h | | |
| Administration Test Example 6 (n = 5) | Example 6 | 416.1 ± 268.9 | 484.7 ± 423.1 | 102.5 ± 38.8 | 593.7 ± 405.6 | 622.8 ± 403.0 |
| Administration Test Example 7 (n = 5) | Example 7 | 1691.2 ± 876.6 | 740.7 ± 328.4 | 222.2 ± 145.3 | 1691.2 ± 876.6 | 1512.2 ± 642.7 |
| Administration Test Example 8 (n = 5) | Example 8 | 2950.2 ± 861.2 | 773.7 ± 201.6 | 340.5 ± 132.9 | 2950.2 ± 861.2 | 2225.6 ± 606.8 |
| Administration Test Example 9 (n = 3) | Example 9 | 708.0 ± 560.6 | 821.3 ± 367.6 | 778.1 ± 710.1 | 944.8 ± 575.6 | 1359.0 ± 901.8 |
| Administration Test Example 10 (n = 3) | Example 10 | 447.7 ± 69.7 | 1003.5 ± 481.6 | 489.6 ± 204.0 | 1003.5 ± 481.6 | 1221.2 ± 491.5 |
| Administration Test Example 11 (n = 3) | Example 11 | 723.3 ± 500.7 | 1180.1 ± 702.4 | 385.5 ± 291.6 | 1180.1 ± 702.4 | 1439.5 ± 921.5 |
| Administration Test Example 12 (n = 3) | Example 12 | 773.6 ± 847.3 | 664.0 ± 512.5 | 892.6 ± 488.3 | 1232.1 ± 590.7 | 1331.1 ± 770.2 |
| Administration Test Example 13 (n = 5) | Example 13 | 799.7 ± 58.3 | 782.6 ± 107.4 | 351.1 ± 62.1 | 1026.9 ± 81.8 | 1162.3 ± 81.5 |
| Comparative Test Example 1 (n = 5) | Curcumin base powder | 7.8 ± 3.0 | 17.2 ± 7.2 | 34.2 ± 7.5 | 49.8 ± 6.6 | 33.9 ± 5.7 |
| Comparative Test Example 2 (n = 5) | Physical mixture (Curcumin:HPMC) | 18.1 ± 13.8 | 28.7 ± 14.8 | 112.9 ± 44.7 | 112.9 ± 44.7 | 87.0 ± 37.9 |
| Comparative Test Example 3 (n = 5) | Physical mixture (Curcumin:HPC) | 15.6 ± 14.2 | 33.6 ± 18.3 | 95.0 ± 48.7 | 95.0 ± 48.7 | 80.5 ± 38.4 |
| Comparative Test Example 4 (n = 5) | CR-031P | 346.8 ± 216.7 | 316.7 ± 209.8 | 306.2 ± 131.0 | 417.4 ± 188.7 | 564.0 ± 292.7 |

TABLE 4

Case with curcumin dose: 50 mg/kg

| | Administered sample | Curcumin concentration in blood plasma (ng/mL) | | | Cmax (ng/mL) | AUC (ng/mL · 0-2 h) |
|---|---|---|---|---|---|---|
| | | 0.5 h | 1 h | 2 h | | |
| Administration Test Example 14 (n = 5) | Example 6 | 3066.3 ± 1190.7 | 1939.7 ± 459.2 | 1295.2 ± 377.3 | 3081.5 ± 1181.2 | 3635.5 ± 712.5 |
| Comparative Test Example 5 (n = 5) | CR-031P | 663.8 ± 336.8 | 410.2 ± 213.8 | 536.8 ± 277.0 | 762.7 ± 332.7 | 908.0 ± 377.5 |

Test Example 2 (Stability of Amorphous Curcumin in Complex)

For the purpose of examining the stability of amorphous curcumin in the various complexes, each of the various complexes (Examples 1 to 5 and 10 to 11) produced as described above was introduced into an aluminum pouch and maintained at 40° C., and the crystallinity of curcumin in these complexes was examined over time (at the initiation of test (0M), one month after the initiation of test (1M), two months after the initiation of test (2M), and four months after the initiation of test (4M), using powder X-ray diffraction apparatus (RINT-ULTIMA III, manufactured by Rigaku Corp.) (FIGS. 6 to 12).

Meanwhile, as the controls, turmeric extract powder (control A: base powder); turmeric extract powder SD product (control B: base powder SD product) obtained by dissolving turmeric extract powder in ethanol and then spray drying the solution under the conditions similar to those for the method described in the section Production Method A; and physical mixtures (controls C1 to 5 and 10 to 11) produced by simply mixing turmeric extract powder and hydroxypropylmethyl cellulose or hydroxypropyl cellulose such that the ratio between curcumin in the turmeric extract and the water-soluble cellulose derivative would be 9:1 to 1:9 as a weight ratio, were used.

These results are presented in FIGS. 6 to 12.

a. Curcumin-Hydroxypropylmethyl Cellulose Complex

In the cases of a complex in which the ratio between curcumin and hydroxypropylmethyl cellulose was 9:1 (Example 1) and a complex in which the ratio was 3:1 (Example 2), peaks indicating the crystallinity originating from curcumin were not recognized at the time of initiation of the test (0M), and curcumin in the complexes was amorphous. In a case in which the complexes were maintained for one month or longer at 40° C. (1M, 2M, and 4M), peaks indicating crystallinity were recognized (FIGS. 6 and 7); however, the peaks were very small.

On the other hand, in the cases of a complex in which the ratio between curcumin and hydroxypropylmethyl cellulose was 1:1 (Example 3), a complex in which the ratio was 1:3 (Example 4), and a complex in which the ratio was 1:9 (Example 5), peaks indicating the crystallinity originating from curcumin were not recognized within the test period, and curcumin in the complexes was amorphous (FIGS. 8 to 10).

From the results described above, it was found that when the ratio between curcumin and hydroxypropylmethyl cellulose (curcumin/hydroxypropylmethyl cellulose) in the curcumin-hydroxypropylmethyl cellulose complex is adjusted to 9/1 to 1/9, particularly to less than 3, curcumin in the complex is maintained in an amorphous state for a long time period.

b. Curcumin-Hydroxypropyl Cellulose Complex

In the case of a complex in which the ratio between curcumin and hydroxypropyl cellulose was 1:3 (Example 10), peaks indicating the crystallinity originating from curcumin were not recognized at the time of initiation of the test (0M), and curcumin in the complex was amorphous. In a case in which the complex was maintained for one month or longer at 40° C. (1M and 2M), peaks indicating crystallinity were recognized (FIG. 11); however, the peaks were very small.

In the case of the complex in which the ratio between curcumin and hydroxypropyl cellulose was 1:9 (Example 11), peaks indicating the crystallinity originating from curcumin were not recognized within the test period, and curcumin in the complex was amorphous (FIG. 12).

From the results described above, it was found that when the ratio between curcumin and hydroxypropyl cellulose (curcumin/hydroxypropyl cellulose) in a curcumin-hydroxypropyl cellulose complex is adjusted to 9/1 to 1/9, particularly to less than 1/3, curcumin in the complex is maintained in an amorphous state for a long time period.

The invention claimed is:

1. A method for producing a complex of (A) curcumin and/or an analog thereof and (B) a water-soluble cellulose derivative selected from the group consisting of hydroxypropylmethyl cellulose, hydroxypropyl cellulose, and a mixture thereof, wherein a weight ratio (A/B) is in a range of 0.02 to 10, the method comprising:
    dissolving the curcumin and/or the analog thereof and the water-soluble cellulose derivative in a water-organic solvent mixed solvent, to obtain a solution; and
    removing water and the organic solvent from the solution.

2. A method for producing a complex of (A) curcumin and/or an analog thereof and (B) a water-soluble cellulose derivative selected from the group consisting of hydroxypropylmethyl cellulose, hydroxypropyl cellulose, and a mixture thereof, wherein a weight ratio (A/B) is in a range of 0.02 to 10, the method comprising:
    dissolving the curcumin and/or the analog thereof in an organic solvent, to obtain a first solution;
    dissolving the water-soluble cellulose derivative in water, to obtain a second solution;
    mixing the first solution with the second solution, to obtain a mixed solution; and
    removing water and the organic solvent from the mixed solution.

3. A complex comprising:
    (A) curcumin and/or an analog thereof, and
    (B) a water-soluble cellulose derivative selected from the group consisting of hydroxypropylmethyl cellulose, hydroxypropyl cellulose, and a mixture thereof wherein the complex is prepared by the method of claim 1 or 2, and a weight ratio (A/B) is in a range of 0.02 to 10.

4. The complex according to claim 3, wherein curcumin and/or the analog thereof comprises curcumin or a turmeric dye.

5. The complex according to claim 3, wherein the water-soluble cellulose derivative is hydroxypropyl cellulose.

6. The complex according to claim 3, wherein the complex is obtained by removing a solvent from a water-organic solvent mixed solution comprising curcumin and/or the analog thereof and the water-soluble cellulose derivative.

7. The complex according to claim 3, wherein curcumin and/or the analog thereof is amorphous.

8. A composition suitable for oral intake, comprising the complex according to claim 3.

9. The complex according to claim 3, wherein the complex comprises curcumin.

10. The complex according to claim 3, wherein the complex comprises the analog of curcumin.

11. The complex according to claim 3, wherein the water-soluble cellulose derivative is hydroxypropylmethyl cellulose.

* * * * *